Figure 1:
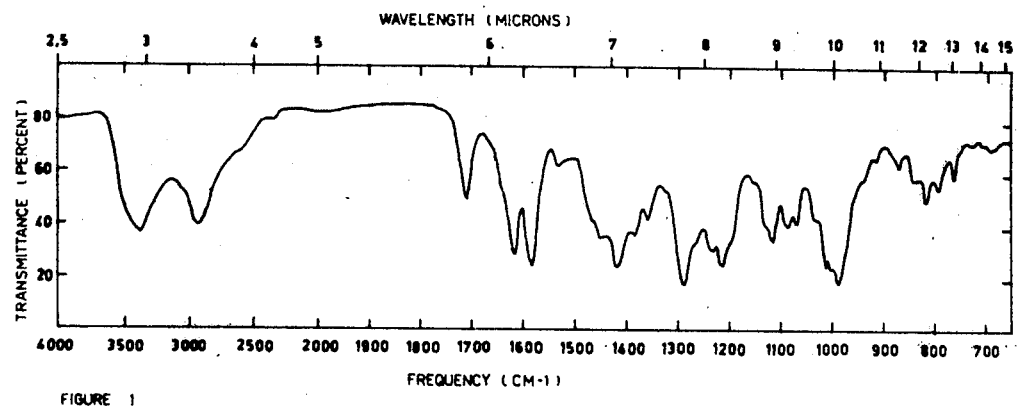

United States Patent [19]

Di Marco et al.

[11] 4,012,284
[45] Mar. 15, 1977

[54] PROCESS OF PREPARATION OF ANTIBIOTIC F.I. 1762 DERIVATIVES

[75] Inventors: Aurelio Di Marco; Graziana Canevazzi; Arpad Grein, all of Milan; Piergiuseppe Orezzi, Rivanazzano Pavia; Marcello Gaetani, Milan, all of Italy

[73] Assignee: Societa' Farmaceutici Italia, S.p.A., Milan, Italy

[22] Filed: Oct. 6, 1964

[21] Appl. No.: 404,550

Related U.S. Application Data

[63] Continuation-in-part of Ser. No. 322,847, Nov. 12, 1963, Pat. No. 3,872,085.

[30] Foreign Application Priority Data

Nov. 16, 1962 Italy .................................. 22651/62

[52] U.S. Cl. .............................. 195/80 R; 424/121; 424/122

[51] Int. Cl.$^2$ ........................................... C12D 9/14
[58] Field of Search .......................... 195/80, 80 R; 167/65 AB; 424/121, 122

Primary Examiner—Jerome D. Goldberg
Attorney, Agent, or Firm—Hubbell, Cohen, Stiefel & Gross

[57] EXEMPLARY CLAIM

1. A process for the preparation of a new antibiotic F.I. 1762, which comprises cultivating the Streptomyces 1762 under aerobic conditions in a liquid nutrient medium containing a carbon source, a nitrogen source and mineral salts, at a temperature between 25° and 37° C, over a period of time from 3 to 7 days, and extracting the formed antibiotic from the fermentation broth at a pH between 8 and 9 by means of a water-immiscible solvent, isolating and purifying the antibiotic F.I. 1762.

3 Claims, 1 Drawing Figure

*INVENTOR.*

*BY*

PROCESS OF PREPARATION OF ANTIBIOTIC F.I. 1762 DERIVATIVES

This is a continuation-in-part of our application Ser. No. 322,847 filed November 12, 1963 now Pat. No. 3,872,085 and relates to a new antibiotic substance and its derivatives, particularly useful as antitumorals as shown on standard experimental animals, and to the process for their preparation. More particularly, the object of the present invention is a new antibiotic of the indicator type, named by us "Daunomycin", which will be called as antibiotic "F.I. 1762". The invention includes its salts, the products of its hydrolytic degradation, and a biosynthetic process for their fermentative preparation by means of a new species of Streptomyces, named by us *Streptomyces peucetius*, which will be called hereinafter "Streptomyces 1762". The productive microorganism, producing the antibiotic F.I. 1762, was isolated from a soil sample taken in the neighborhood of Bari (Italy) and shows the following morphologic, macroscopic, microscopic and biochemic characteristics. Streptomyces F.I. 1762 has been deposited at the Commonwealth Mycological Institute, Ferry Lane, Kew, Surrey (Great Britain) receiving the index number I.M.I. 101,335, and at the National Collection of Industrial Bacteria, Aberdeen (Great Britain) receiving the index number NCIB 9475, and at the Institute of Microbiology of the Rutgers University (U.S.A.) receiving the index number IM 3868.

MICROSCOPIC ASPECT

The vegetative mycelium on the usual culture media consists of thin hyphae (0.5–0.9 $\mu$ thickness) more or less long, and branched. The ramifications bear thicker hyphae (1.1–1.6 $\mu$ thick), the conidiophores, frequently fasciculated and ending in hooks and loops. The conidia are spherical and of a diameter between 1.8–3.3 $\mu$, first disposed in little chains and then free. Under the electron microscope, the conidia are nearly spherical, of irregular surroundings, with a warty surface.

MACROSCOPIC ASPECT

In Table I, the cultural characteristics observed on the media therein indicated are reported, in which the microorganism is grown at 28° C and the observations are made at the 3rd, 8th, 15th, 21st and 30th day after the inoculation.

BIOCHEMICAL PROPERTIES

Gelatin: slow and partial hydrolysis.
Nitrates: no reduction to nitrates.
Production of $H_2S$: positive.
Milk: no peptonization, no coagulation.
Starch: slow and slight hydrolysis.
Maltose, xylose, mannose, mannitol, glycerol, glucose, saccharose, trehalose, raffinose, fructose are utilized, whereas lactose, adonitol, ramnose, sorbitol, arabinose and esculine are not utilized.
Antibiotics: it produces antibiotic substances in liquid submerged culture.

Table I

| Cultural properties of "Streptomyces F.I. 1762" | | | | |
| --- | --- | --- | --- | --- |
| Media | Growth | Aerial mycelium | Vegetative mycelium | Soluble pigments |
| Malt-yeast extract agar (according to Hesseltine et al) (°) | Little confluent colonies with wrinkled folds, hard, relieved, abundant | Very scarce, smooth, pale rose colored. Absence of spinals and verticils | Abundant, yellowish, then yellow-reddish | Intense, first yellow-red then red-brown |
| Bennet Agar | Scanty, single yellowish little colonies | Absent | Scanty, first whitish then yellowish | Absent |
| Emerson Agar | Moderate in little confluent colonies | Absent | Moderate, first pale rose then brownish reddish | Reddish to pale brown |
| Potato Agar (according to Hesseltine et al) (°) | Abundant, in smoothed uniform patina | Abundant, rose. Hook-ended and then loops-ended hyphae | Abundant, flesh-colored. Smoothed, hard patina | Intense, first yellow-reddish then dark orange |
| Peptone Agar + $KNO_3$ | Abundant, in confluent little colonies | Absent | Abundant, colorless | Absent |
| Szapeck Agar | Abundant, in confluent little colonies | Scanty, dirty white, cottony. Hook- and loops-ended hyphae | Abundant, pale rose colored | Absent |
| Asparagine-glucose | Scanty, and in little single colonies | Scanty, whitish rose. Very broken mycelium, short, without apical hooks | Colorless | Absent |
| Glycerin-glycine Agar | Abundant, in smoothed hard patina | Absent | Abundant from yellow to light orange | Absent |
| Amid-Agar | Scanty, in | Absent | Scanty, | Absent |

Table I-continued

Cultural properties of "Streptomyces F.I. 1762"

| Media | Growth | Aerial mycelium | Vegetative mycelium | Soluble pigments |
|---|---|---|---|---|
| Gelatin | single little colonies Moderate, in surface | Absent | colorless then yellow rose Moderate, from colorless to yellow | Abundant, brown dark black |
| Milk | Scanty | Absent | Ring-formed in surface, rose-salmon-colored | Scanty, rose |

(*) Hesseltine et al 1954 Ann. N.Y. Acad. Sci.60, S. 136 – 151

Table II

Comparison of Streptomyces F.I. 1762 and productive species of substances similar to the antibiotic F.I. 1762

| | Streptomyces F.I. 1762 (S.peucetius) | S.purpurascens | S.bobiliae | S.cinereoruber | S.cinereoruber, var. fructo-fermentans | S. caospitosus |
|---|---|---|---|---|---|---|
| Sperophores | straight or hooked-like | spirally | spirally | straight or hooked-like | straight or hooked-like | vertically |
| Spores | roundish warty 1.8–3.3 $\mu$ | oval spiny 0.8–1 $\mu$ for 0.4–0.5 $\mu$ | / | oval, smooth 0.7–1 $\mu$ for 0.9–2 $\mu$ | oval smooth 0.7–1 $\mu$ for 0.9–2 $\mu$ | oval smooth 0.5–1.3 $\mu$ for 0.3–0.5 $\mu$ |
| Vegetative mycelium | yellow-red | red | coral red | yellow-red brown | yellow-red brown | from cream-color to brown to yellow-reddish |
| Aerial mycelium | white-rose | white-rose | white | ash-gray | ash-gray | white yellowish gray |
| Reduction of nitrates | − | / | + | / | / | + |
| Milk (peptonization coagulation) | − | − | + | + | + | + |
| L-xylose | + | + | + | + | + | − |
| L-arabinose | − | + | + | + | + | − |
| L-ramnose | − | + | + | − | + | − |
| Fructose | + | + | + | − | ++ | |
| Saccharose | + | + | + | − | + | + |
| Lactose | − | + | + | + | + | / |
| Raffinose | + | + | + | − | − | − |
| D-mannite | + | + | − | − | + | − |
| D-sorbite | − | − | − | − | + | + |
| Antibiotics produced | Daunomycin or Antibiotic F.I. 1762 | Rodomycine | Cynerubine | Rodomycine | Cynerubine | Mitomycine |

| | S.niveoruber | S.antibioticus | 380, 1954) | Streptomyces A 1165 (Ashashev et al: Antib. and Chemoth.4 380, 1954) | Streptomyces A 220 (Ashashev et al: Antib. and Chemoth.4 1880, 1959) | Streptomyces DOA 1205 (Brockmann: Chem. Ber. 92, |
|---|---|---|---|---|---|---|
| Sperophores | Spirally | spirally | straight | not described | not described | spirally |
| Spores | smooth | smooth | smooth spheric | not described | not described | not described |
| Vegetative mycelium | carmin red | carmin red | yellow-creamy | not described | not described | brick-red wine-red |
| Aerial mycelium | whitish | from white to ash-gray | from white to mouse-gray | not described | not described | red-gray |
| Reduction of nitrates | / | / | / | / | / | / |
| Milk (peptonization coagulation) | − | + | + | / | / | + |
| L-xylose | / | / | / | / | / | / |
| L-arabinose | / | / | / | / | / | / |
| L-ramnose | / | / | / | / | / | / |
| Fructose | / | / | / | / | / | / |
| Saccharose | / | / | / | / | / | / |
| Lactose | / | / | / | / | / | / |
| Raffinose | / | / | / | / | / | / |
| D-mannite | / | / | / | / | / | / |
| D-sorbite | / | / | / | / | / | / |
| Antibiotics | Cynerubine | Cynerubine | Cynerubine | Aklavine | Rutilantine | Pyrromycine |

Table II-continued

Comparison of Streptomyces F.I. 1762 and productive species of substances similar to the antibiotic F.I. 1762 produced + = positive reaction
− = negative reaction
/ = data is lacking

IDENTIFICATION OF THE STRAIN

The description of the microorganism relates to the genus *Streptomyces Wakaman and Henriei* (Bergey's Manual of Determinative Bacteriology, Seventh Edition (1957) pages 744–745). From examination of the species it may be concluded: in the classification system of Pridham et al (Appl. Microbiol. 6, 1958, page 52) the microorganism belongs to the section *Retinaculum apertum*, series RED. In the classification system of Baldacci (Giorn. di Microbiol. 6, 1958, page 10) the microorganism belongs to the series Albosporeus; finally in the system of Waksman (The Actinomycetes, Vol. II, 1961, page 129) the microorganism belongs to the series Ruber.

A comparison between the characteristics of the microorganism and those of species belonging to systematic cited groups (Taxa), demonstrates that none of them have characteristics corresponding to those of the microorganism under examination. Table II lists the comparison data concerning the species which produce substances similar to those studied by us. In that table there are added *S. cinerooruber*, *S. cinereoruber var. fructo-fermentans*, *S. caespitosus* and *S. antibioticus*, also if they are not part of the above-cited Taxa.

Included herewith is a list of differences from species which do not produce substances of the studied type. *Streptomyces F.I.* 1762 (our microorganism) differs from *S. albosporeus* (Waksman : The Actinomycetes, Vol. II, 1961, page 171), because the latter does not produce soluble pigments, does not reduce the nitrates and does not produce $H_2S$; from *S. cinnamomensis* (Waksman, The Actinomycetes, Vol. II, 1961, pages 195–196) and from *S. fradiae* (Waksman: The Actinomycotes, Vol. II, 1961, pages 211–212) in the color of the vegetative and aerial mycelium; from the species *S. ruber* (Waksman: The Actinomycetes, Vol. II, 1961, page 271) because the latter coagulates milk, does not produce soluble pigments and does not produce $H_2S$; from *S. rubescens* (Waksman: The Actinomycetes, Vol. II, 1961, page 271) because of the color of the aerial mycelium and because *S. rubescens* does not produce soluble pigments nor hydrogen sulphide; from *S. oidiosporus* (Waksman: The Actinomycetes, Vol. II, 1961, page 251) because the latter does not reduce nitrates, does not peptonize milk nor produce soluble pigments.

It is concluded that the *Streptomyces F.I.* 1762 should be considered a species different from those known up to the present and therefore it has been given the binomial *Streptomyces peucetius n.sp.*

The microorganism Streptomyces F.I. 1762 may be stored by lyophilization, milk or milk serum being the suspending medium, by collecting and keeping the spores in a sterile substrate. Moreover, it may also be stored by successive cultivations on a solid medium containing glucose, or an other suitable sugar and complex substances containing nitrogen (yeast extract, peptone, hydrolyzed casein). The culture medium may also contain some salts, among which are magnesium sulphate and potassium phosphate.

The production of the antibiotic may be performed according to the usual well known methods and consists in cultivating the Streptomyces 1762 or mutant thereof in a liquid nutrient medium, containing assimilable carbon and nitrogen, which medium was previously sterilized at a temperature between 25° and 37° C, preferably at 28° C. The cultivation occurs under aerobic conditions over a period of time from 3 to 7 days, preferably 5 days, at a pH which initially is 6.5–7.0 and finally is 7.5–8.0. The culture medium consists of a carbon source and a nitrogen source as well as of salts.

The carbon source may be for example starch, dextrin, glucose, glycerin, mannito, maltose, corn steep liquor, distillers solubles, soy-bean oil, or soy-bean meal. The nitrogen source, besides the above-cited complex substances containing nitrogen, may for example be dry yeast, meat peptone, casein. Good results are achieved by employing ammonium salts, such as ammonium nitrate, ammonium sulphate, or biammonium phosphate. The mineral salts useful for the production of the antibiotic may vary according to the employed medium. In a medium containing complex substances, such as various meals and fermentation residues, the additions of calcium carbonate and sodium- or potassium phosphate have proved useful. In media containing glucose, yeast or ammonium salts, some addition of mineral salts, such as potassium, magnesium, iron, zinc, manganese or copper salts, is necessary.

The fermentation may be carried out in Erlenmeyer flasks or in laboratory or industrial fermenters of various capacity. The quantity of antibiotic F.I. 1762 in the broth may be evaluated by spectrophotometric checking of the hydroalcohol extracts of said broth at pH 10, at 540–580 m$\mu$ and in comparison with a sample having a known content in F.I. 1762.

In order to isolate the antibiotic F.I. 1762, the mycelium may be separated from the culture liquid by means of a filtering coadjuvant containing an adsorbent siliceous earth material and treating the filtration cake and the filtrate separately. Most of the antibiotic is to be found in the filtration cake consisting of the mycelium, admixed to the adsorbent siliceous earth material. The mass is pulped and stirred in an organic solvent, such as methanol, ethanol, butanol; in ketones, such as acetone, methylethylketone; halogenated hydrocarbons, such as chloroform, methyl chloride or aqueous solutions of organic and inorganic acids: such as acetic acid, hydrochloric acid, or sulphuric acid. Mixtures of organic solvents, such as alcohols and water-miscible ketones and aqueous solutions of inorganic acids may be used advantageously.

When mixtures of organic solvents and aqueous acid solutions are used, the extracts are neutralized and the organic solvent is eliminated in vacuo, until an aqueous suspension is obtained. The precipitate, formed during concentration, is filtered off. The filtrate is made alkaline at at pH between 8 and 9 and extracted with a solvent immiscible with water, such as butyl alcohol, amyl alcohol; halogenated hydrocarbons such as chloroform, methyl chloride; ketones such as methyl-propyl-ketone, methyl-butyl-ketone; hydrocarbons such as benzene, toluene and their analogues.

When low-boiling water-miscible organic solvents are used in the extraction, they are mixed with water and concentrated in vacuo to remove the organic solvent. The aqueous phase is extracted as described in the preceding case. From the water-immiscible organic solution, the active crude substance is obtained by concentration to a small volume and precipitation with low-polar solvents as ethers, such as ethyl ether, dipropyl ether, saturated by hydrocarbons, e.g. hexene, cyclohexane, heptane or petroleum ether. The resultant solution contains other pigmented substances, which may be extracted with alkaline aqueous solutions containing inorganic or organic alkalis and said pigmented substances may be obtained in solid state by acidification of the aqueous solution. It is advantageous to operate a first purification of the antibiotic, by extracting the organic solution with organic or inorganic dilute aqueous acids, such as acetic acid, hydrochloric acid, sulphuric acid, at a pH between 2 and 5, or with a buffer solution at a pH value in this range. In order to facilitate the transfer of the antibiotic into the aqueous phase, it is advantageous to add to the organic phase a few volumes of a low polar solvent, such as ethyl ether, diisopropyl ether; a saturated hydrocarbon, such as hexane, cyclohexane, heptane or petroleum ether. In the organic phase there remain different other pigmented products, whose nature has not yet been studied.

The pH of the resulting aqueous phase is kept between 8 and 9 and it is reextracted with organic solvents, such as butyl alcohol, amyl alcohol; a halogenated hydrocarbon, such as chloroform, methyl chloride; a hydrocarbon such as benzene and toluene; a phenol such as phenol or cresol. The extract thus obtained is then concentrated in vacuo to a small volume, and the precipitation of the crude antibiotic in form of salt is achieved by adding an organic or inorganic acid and a low polarity solvent, such as ethyl ether, diisopropyl ether, a saturated hydrocarbon, such as cyclohexane, hexane, heptane or petroleum ether.

A good purification of the crude materials thus obtained may be carried out by countercurrent distribution of an aqueous solution, such as aqueous acid or a buffer solution and a water-immiscible solvent. Chromatography is also a useful purification means.

A separation method of the antibiotic may consist in treating an aqueous solution of one of its salts with picric acid. The picrate of the antibiotic precipitates in red-yellow flakes, which are collected and dried. The picrate is soluble in lower aliphatic alcohols, halogenated hydrocarbon: for instance chloroform; ketones: for instance acetone, methylethylketone. By treating the organic solution of the picrate with an organic acid, the salt of the antibiotic separates.

The antibiotic occurs as dark red crystals melting at 208°–209° C. It is soluble in alcohols, ketones, halogenated hydrocarbons, aqueous solutions of organic and inorganic acids, slightly soluble in water and practically insoluble in ethers and saturated hydrocarbons.

The antibiotic F.I. 1762 crystallizes as hydrochloride in little red needles. The hydrochloride is soluble in water, methanol, aqueous alcohols; it is insoluble in chloroform, acetone, benzol and non-polar solvents. Perfectly dried it melts at 188–190° C and has the composition $C_{27}H_{29}O_{10}N.HCl$; $[\alpha]_D^{25} = +253°$ (c = 0,15, methanol).

Its adsorption spectrum in U.V. and in the visible ranges is very similar to 1,4,5-trihydroxyanthraquinone and presents bands in the following wave lengths:
in absolute methanol:
at 234 m$\mu$ $E_{1cm}^{1\%}$ = 632
251 " " " = 454
290 " " " = 149
480 " " " = 203
495 " " " = 208
532 " " " = 116
in concentrated $H_2SO_4$: at 257, 303, 545 and 585 m$\mu$.
In the I.R. spectrum (see FIG. 1 in the enclosed drawing table) are visible bands in the following wave lengths:

| | | | |
|---|---|---|---|
| 2.96 $\mu$ | 7.05 $\mu$ | 8.96 $\mu$ | 12.20 $\mu$ |
| 3.42 " | 7.23 " | 9.27 " | 12.68 " |
| 5.82 " | 7.37 " | 9.35 " | 13.12 " |
| 6.17 " | 7.78 " | 10.10 " | 13.77 " |
| 6.31 " | 8.11 " | 10.92 " | 14.20 " |
| 6.51 " | 8.24 " | 11.50 " | 14.60 " |
| 6.90 " | 8.65 " | 11.85 " | |

The aqueous solutions are yellow-red and turn to violet by alkalinization. With magnesium acetate, they show a red-crimson coloring. On hydrolysis with dilute mineral acids, the antibiotic F.I. 1762 decomposes into a reducing sugar (daunosamine) and a neutral aglycone. The aglycone, called daunomycinone, forms brilliant red crystals, has the composition $C_{21}H_{18}O_8$ melting at 213°–214° C, $[\alpha]_D^{25} + 193°$ (c 0.1, dioxane) and one $OCH_3$.

The absorption spectra in the U.V. and in the visible ranges give, with the different employed solvents, adsorption maxima at the following wave lengths:
in absolute methanol:
at 234 m$\mu$ $E_{1\ cm}^{1\%}$ = 782
251 m$\mu$ $E_{1\ cm}^{1\%}$ = 568
288 m$\mu$ $E_{1\ cm}^{1\%}$ = 186
480 m$\mu$ $E_{1\ cm}^{1\%}$ = 258
496 m$\mu$ $E_{1\ cm}^{1\%}$ = 267
532 m$\mu$ $E_{1\ cm}^{1\%}$ = 149
in concentrated $H_2SO_4$: at 257, 303, 545, 585 m$\mu$ (inflection point at 390 m$\mu$).
in anhydrous piperidine: at 540, 570 and 610 m$\mu$.

Figure 2:
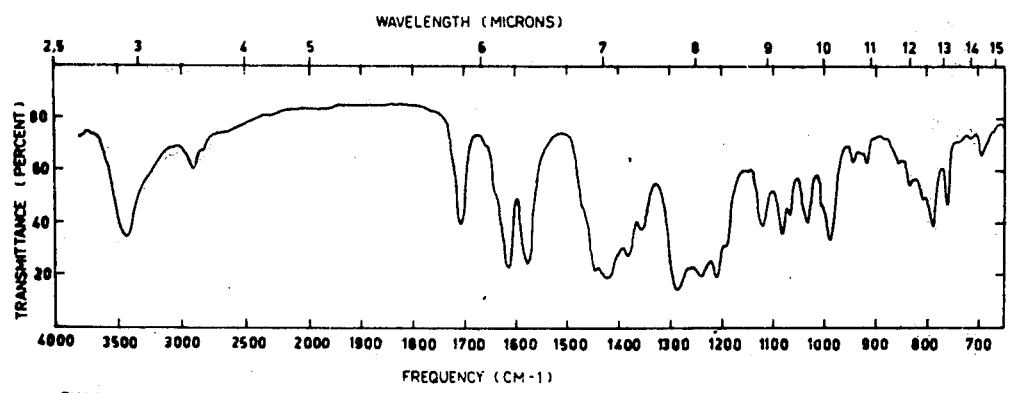

In the I.R. spectrum (see FIG. 2) bands of the following wave lengths are noted (in $\mu$); 2.90, 3.42, 5.85, 6.18, 6.33, 6.90, 7.03, 3.24, 7.35, 7.75, 8.06, 8.25, 8.94, 9.37, 9.67, 10.10, 10.59, 10.91, 11.68, 11.99, 12.35, 12.63, 13.18, 14.40.

Daunomycinone, the aglycone of the antibiotic, is soluble in methanol, ethanol, chloroform; less soluble in butanol, acetone; scarcely soluble in benzene, aliphatic esters, ethyl ether; insoluble in water, petroleum ether. The aglycone is also present in the crude antibiotic obtained with the described methods. It may be shown by paper chromatography with developer n-butanol saturated with aqueous phosphate buffer at pH 5.2.

Daunomycinone displays the same electronic spectrum as the parent glycoside. Zinc dust distillation gives tetracene, thus establishing for the aglycone the tetracyclic structure already found in the tetracyclines and antracyclines. The presence of an aliphatic ketonic group, in addition to the chelated quinone system (1617 cm$^{-1}$), is indicated by the absorption band at 1718 cm$^{-1}$ in the infrared and by the ready formation of a 2,4-dinitrophenylhydrazone. The nuclear magnetic resonance spectrum (CF$_3$COOH) shows one OCH$_3$ (singlet, 4.04 δ), one COCH$_3$ (singlet, 2.69 δ), broad absorptions at 3.27 δ (2H), 2.67 δ (2H), 7.1-7.9 δ (three arom. H) and a signal at 5.50 δ (1H, broad) attributed to a proton on a benzylic carbon bearing a hydroxyl group, because of its downfield shift (6.40δ) on acetylation.

By refluxing with dimethyl sulfate in acetone in the presence of potassium carbonate daunomycinone is converted to a trimethyl ether C$_{24}$H$_{24}$O$_8$, m.p. 193° C, four OCH$_3$, $[\alpha]_D^{25}$ + 181° (c 0.1 in dioxane), exhibiting a hydroxyl band at 3350 cm$^{-1}$. The n.m.r. spectrum of this compound shows four sharp singlets at 4.00δ (6H, two arom. OCH$_3$), 3.89 δ (3H, arom. OCH$_3$), 3.56 δ (3H, aliphatic OCH$_3$), 2.40 δ (3H, COCH$_3$); a free hydroxyl group (singlet, 5.02 δ)is clearly recognized by the upfield shift with dilution and downfield shift with acid. A signal at 4.92 δ (1H, four lines), showing the Ar-CH-O proton, is the X part of an ABX spectrum, the AB part of which consists of two pairs of symmetric doublets centered approximately at 1.87δ (1H) and 2.42 δ (1H); a first order analysis gives J$_{AB}$ = 15 ± 0.2, J$_{AX}$ = 3.5 ± 0.2 and J$_{BX}$ = 2.5 ± 0.2 c.p.s. The magnitude of the J$_{AB}$, characteristic of a geminal coupling, and the shifts of H$_A$ and H$_B$ are indicative for a methylene β to an aromatic ring. Two doublets (2H, J = 18.5 ± 0.2 c.p.s.) centered at 3.02 δ and 3.22 δ, characteristic of an AB pattern, indicate two geminal protons α to the aromatic system, without vicinal hydrogens. A complex multiplet (ABC pattern) between 7–8 δ (3H) suggests three aromatic protons on the same ring. This observation is in agreement with the recovery of salicylic acid by alkaline fusion of either daunomycinone or its trimethylether.

All these facts indicate structure I (a or b) for the trimethylether of daunomycinone.

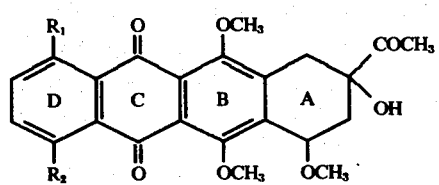

I a: R$_1$ = H, R$_2$ = OCH$_3$
I b: R$_1$ = OCH$_3$, R$_2$ = H

The presence of four hydroxyls in daunomycinone was proved by the conversion, on treatment with acetic anhydride in pyridine at 60° C, to a tetraacetate C$_{29}$H$_{26}$O$_{12}$, one OCH$_3$, m.p. 225° C (from methanol), $[\alpha]_D^{25}$ − 95.5° (c 0.11, CHCl$_3$), phenolic (1776 cm$^{-1}$) and alcoholic (1740 cm$^{-1}$) acetate bands, no hydroxyl absorption in the infrared. Daunomycinone is converted by treatment with either acids or alkalis to a bisanhydro derivative C$_{21}$H$_{14}$O$_6$, m.p. 225°–30° C, conjugated ketone absorption at 1685 cm$^{-1}$ in the infrared, which in turn yields a diacetate C$_{25}$H$_{18}$O$_8$, m.p. 240°–3° C, one OCH$_3$, phenolic acetate absorption (1765 cm$^{-1}$), thus proving the presence of two phenolic and two alcoholic hydroxyls in daunomycinone, the last two being involved in the dehydration reaction of ring A. A similar tendency to full aromatization is displayed by the rhodomycinones and related anthracyclinones.

The benzylic hydroxyl is removed by catalytic reduction of daunomycinone with Pd on BaSO$_4$ is dioxane, affording deoxydaunomycinone C$_{21}$H$_{18}$O$_7$, m.p. 229°–231° C, $[\alpha]_D^{25}$ − 91° (c 0.11, CHCl$_3$), one OCH$_3$. The n.m.r. spectrum (CDCl$_3$) shows, in addition to OCH$_3$ (4.05δ) and COCH$_3$ (2.35 δ), two sharp singlets at 13.3 δ (1H) and at 13.75δ (1H) due to the two strongly hydrogen bonded phenolic OH, a signal at 3.75δ (singlet, 1H, free alcoholic OH), broad absorption at ca. 3δ (two benzylic CH$_2$), at ca. 2δ (CH$_2$β to the arom. ring) and at ca. 8 δ (3H, arom.protons). Deoxydaunomycinone yields a triacetate C$_{27}$H$_{24}$O$_{10}$, m.p. 126°–128° C.

Sodium borohydride reduction followed by periodate oxidation yields acetaldehyde, isolated as the 2,4-dinitrophenylhydrazone, in good yield, thus proving the acetylic side chain and its attachment to a hydroxylated carbon atom. Oxidative fission with permanganate of ring B and C yields almost quantitatively 1,2,4-benzenetricarboxylic acid (trimellitic acid), m.p. 216°–219° C (from ring A), and 3-methoxyphthalic acid, m.p. 168°–171° C (from ring D), both identical in all respects to authentic samples. The latter acid shows the presence of the methoxyl group at C$_7$ or C$_{11}$ on ring D.

Structure II (a or b) and III (a or b), aside from stereochemistry, can now be written for daunomycinone and for bis-anhydrodaunomycinone respectively.

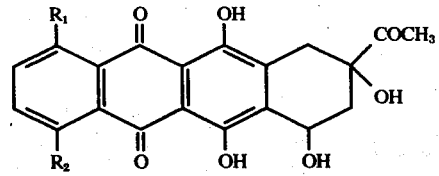

IIa: R$_1$ = H, R$_2$ = OCH$_3$
IIb: R$_1$ = OCH$_3$, R$_2$ = H

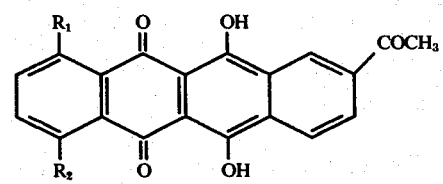

IIIa: R$_1$ = H, R$_2$ = OCH$_3$
IIIb: R$_1$ = OCH$_3$, R$_2$ = H

The aminosugar moiety (daunosamine) as indicated above is obtained by mild acid hydrolysis of the antibiotic F.I. 1762 and is isolated as the hydrochloride C$_6$H$_{13}$O$_3$N . HCl, m.p. 168° dec., $[\alpha]_D^{25}$ at equilibrium −54.5° (c 1.0, H$_2$O). It is a reducing (positive Fehling, Tollens) amino (positive Elson-Morgan, ninhydrin) trideoxyhexose, yielding ammonia on treatment with hot alkalis. Acetylation of daunosamine (IV) with acetic anhydride and pyridine gives a crystalline mixture of the anomeric triacetate (V), m.p. 168°–170° C, $[\alpha]_D^{25}$ −71° (c 0.5, acetone).

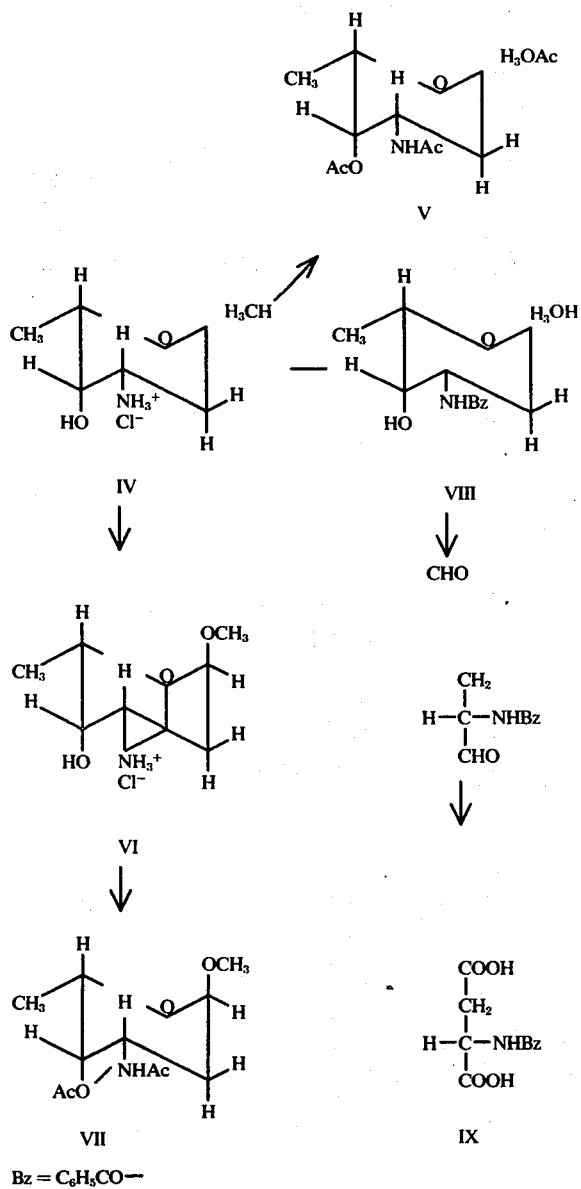

Bz = C₆H₅CO—

The recovery of malonic dialdehyde, identified by the reaction with thiobarbituric acid, and of acetaldehyde, isolated as the 2,4-dinitrophenylhydrazone, among the products of the periodate oxidation of IV, indicates the presence of the desoxy group at C-2 (or C-3) and of the methyl groups at C-5. The latter is also indicated by the fact that IV gives a positive iodoform test.

As other known 2-desoxysugars, IV is readily converted by treatment with 0.3 N methanolic HCl to α-methyldaunosaminide (VI), m.p. 188°–190° dec., $[\alpha]_D^{25}$ −130° (c 0.6, H₂O), which gives an N,O-diacetate (VII), m.p. 176°–178° C, $[\alpha]_D^{25}$− 130° (c 1.0, CHCl₃), when treated with acetic anhydride and pyridine. VI reduces one mole of periodate, thus proving the pyranose ring, the desoxy groups at C-2, and the attachment of the amino and hydroxyl groups at C-3 and C-4. VII is not oxidized by periodate.

The position of the amino group is shown by the results of the periodate oxidation of N-benzoyldaunoxamine (VIII), m.p. 154°–156° C, $[\alpha]_D^{25}$−107.5° (c 1.0, ethanol). This compound reduces one mole of the reagent, yielding acetaldehyde, originated from C-5 and C-6, and a non-volatile aldehyde, which is oxidized to N-benzoyl-L-(+)-aspartic acid (IX), $[\alpha]_D^{25}$+33° (c 0.5, H₂O plus two equivalents of KOH), identical by m.p., mixed m.p., infrared spectrum, chromatographic behavior and optical rotation, to an authentic sample. This compound, that originates from C-1 to C-4 of VIII, establishes the absolute configuration at C-3 as S.

Molecular rotation of IV ($M_D$ = 100), almost identical to that of rhodosamine hydrochloride ($M_D$ = 102), has been compared with the $M_D$ values of the equilibrium mixtures of the α and β forms of the eight stereoisomeric 2,6-dideoxyhexoses. Only the L-lixo (2-deoxy-L-fucose) and the L-ribo (L-digitoxose) compounds show $M_D$ values (−91 and −68 respectively) approaching that of IV. However, IV cannot have the L-ribo configuration, because of the spatial arrangement at C-3; therefore the L-lixo configuration is suggested by the optical rotation data.

The nuclear magnetic resonance spectrum (CDCl₃) of VII shows a triplet at 4.75 δ (H-1), the small splitting of which (in first approximation $J_{1e,2e} = J_{1e,2a} = 2.0$ c.p.s.) indicates the equatorial orientation of the anomeric proton. The NH absorption appears as a doublet (J = 8 c.p.s.) at 5.85 δ, that disappears with D₂O; a broad absorption at 4.45 δ is attributed to the H-3, near to the amidic proton. The H-4 signal at 5.02 δ is a quartet with splitting 1.5 and 2.5 c.p. s; the H-5 quartet at 4.00 δ is further split to an octet (J = 1–1.5 c.p.s.) by H-4. The small coupling constants between H-5, H-4 (ca.1 c.p.s.) and between H-4, H-3 (2.5 c.p.s.) exclude a diaxial orientation between the said protons, whereas the width of the H-3 signal suggests an axial orientation of this proton.

The shifts of the acetoxy (2.16δ) and acetamido (1.91 δ) groups are in good agreement with an axial —OAc at C-4 and an equatorial —NHAc at C-3. Consequently configuration S has to be assigned to C-4. The methyl group at C-5 cannot be axial (D configuration), because in this case VII would exist in the more stable C-1 conformation which is not in agreement with the values of the coupling constants.

Stereochemistry of daunosamine is thus established as 3(S), 4(S), 5(S), corresponding to the L-lixo configuration, as shown in structure IV.

A paper chromatography-system n.butanol saturated with aqueous phosphate buffer at pH 5.2 the antibiotic F.I. 1762 has a Rf = 0,21, the aglycone thereof has Rf=0.85. The antibiotic F.I. 1762 belongs to the group of antibiotics, part of which are rodomycine A, B and γ (H. Brockmann et al, Chem. Ber. 88 1955, page 1762, Naturwissenschaften 48 1961, page 716), cynerubine (Chem. Ber. 92, 1959, page 1868), pyrromycine (Chem. Abstracts 54, 1960, page 1470) and rutilantine (Tetrahedron Letters 16, 1959, page 17). Nevertheless the antibiotic F.I. 1762 differs from the above products in the chemical-physical properties, especially in I.R. and U.V. spectra and in the chromatographic behavior.

Non-toxic acid addition salts of the antibiotic F.I. 1762 may be derived from organic and inorganic non-toxic acids, such as hydrochloric acid, sulphuric acid, acetic acid, propionic acid, valerianic acid, palmitic acid, oleic acid, citric acid, succinic acid, mandelic acid, glutamic acid, pantothenic acid. Neutral salts may be formed by reacting the corresponding acid with the free base, which may be obtained by adjusting at pH 8.6 an aqueous solution of the hydrochloride and by extracting with water-immiscible organic solvents, such as butanol or chloroform. By evaporation of the organic solvent the antibiotic, as free base melting at 208°–209° C, is obtained. Salts may also be obtained by a double decomposition of salts: for instance from F.I. 1762 phosphate and calcium pantothenate, F.I. 1762 pantothenate is obtained. The antibiotic F.I. 1762, besides having a remarkable bacteriostatic activity against several microorganisms, has proved particularly useful as antitumoral as shown on standard experimental animals.

The spectrum of antibiotic F.I. 1762 embraces grampositive, gram-negative bacteria, fungi and protozoa as hereinbelow indicated:

| Microorganismus | concentration | activity (in vitro) |
|---|---|---|
| Staphylococcus aureus | 100γ/cc | + |
| Sarcina tetragena | 100γ/cc | + |
| Streptococcus faecalis | 1000γ/cc | + |
| Mycobacterium species 607 ATCC | 100γ/cc | + |
| Nocardia asteroides | 1000γ/cc | + |
| Escherichia coli 9637 ATCC | 100γ/cc | − |
| Shigella flexneri | 100γ/cc | − |
| Klebsiella pneumoniae | 100γ/cc | − |
| Proteus vulgaris | 1000γ/cc | + |
| Debaromyces marylandii | 100γ/cc | + |
| Trichophyton mentagrophytes | 100γ/cc | + |
| Trichomonas foetus | 100γ/cc | + |

As antitumoral the antibiotic F.I. 1762 shows a marked inhibitory effect on the tumor growth in ascitic form, in which an immediate contact of the antibiotic and the neoplastic cells is achieved. Good inhibiting effect is observed also in solid tumors where the activity is different according to the administration route and to the dose. The best results are achieved by intravenous administration of doses between 2 and 3 mg/kg/body weight day.

In the following Table the acute toxicity of Daunomycin as $LD_{50}$ is reported.

| Acute Toxicity - $LD_{50}$ Values (mg/kg) | | |
|---|---|---|
| Animal species | Route | $LD_{50}$ mg/kg |
| Mouse | intravenous | 20 |
| Mouse | intraperitoneal | 5 |
| Rat | intravenous | 13 – 15 |
| Rat | intraperitoneal | 8 |

The antibiotic F.I. 1762 and derivatives thereof, the products of its hydrolytic cleavage and the mixture thereof may be used as medicine. These contain the specific compounds in admixture with pharmaceutical carriers suitable for oral, parenteral or local administration. Said excipients may be gelatin, lactose, starch, talc and other substances usually employed for this purpose. The pharmaceutical preparations can exist in the form of tablets, dragees, powders, salves, creams, suppositories and in liquid form, such as solutions, suspensions, or emulsions in ampoules for parenteral administration.

The following examples serve to illustrate the invention without limiting it.

EXAMPLE 1

Two 300 ml Erlenmeyer flasks, each containing 60 ml of the following vegetative medium, are prepared:
Peptone: 0.6%
Dry yeast: 0.3%
Calcium nitrate hydrate: 0.05%
in tap water The pH after sterilization is 7.2. The sterilization is carried out by heating in an autoclave to 120° C for 20 minutes.

Each flask was inoculated with mycelium of Streptomyces 1762 whose quantity corresponds to 1/5 of a suspension in sterile water of the mycelium of a 10 days' old culture grown in a test tube containing the following medium:
Saccharose: 2%
Dry yeast: 0.1%
Potassium hydrogen phosphate: 0.2%
Sodium nitrate: 0.2%
Magnesium sulphate: 0.2%
Agar: 2%
in tap water The flasks are incubated at 28° C for 48 hours on a rotary shaker with a stroke of 60 mm at 220 r.p.m. 2 ml of a vegetative medium thus grown are used to inoculate Erlenmeyer flasks of 300 ml with 60 ml of the following productive medium:
Glucose: 4%
Dry yeast: 1.5%
Sodium chloride: 0.2%
Potassium hydrogen phosphate: 0.1%
Calcium carbonate: 0.1%
Magnesium sulphate: 0.01%
Iron sulphate: 0.001%
Zinc sulphate: 0.001%
Copper sulphate: 0.001%
in tap water
pH: 7.0

This is sterilized at 120° C for 20 minutes. The glucose was previously sterilized separately at 110° C for 20 minutes. It is incubated at 28° C under the same conditions described for the vegetative media. After 120 hours of fermentation the maximum activity corresponding to a concentration of 60 μg/ml is achieved.

EXAMPLE 2

The operation is carried out as in Example 1 with the difference that the inoculating culture is grown on the following solid medium: 200 g of peeled potatoes are boiled for 20 minutes in 500 ml of water; the volume is brought to its original value and filtered through gauze. 2% of glucose, 0.1% of extract of Difco yeast and 2% of agar are added. It is brought to 1000 ml and sterilized at 120° C for 20 minutes, pH 6.8–7. The maximum of activity, 70 μg/ml, is achieved after 140 hours.

EXAMPLE 3

The operation is carried out as in Example 2 with the difference that the vegetative and productive media have the following compositions:
Vegetative medium:
Dextrin: 3%
Calcium carbonate: 0.4%
Corn steep liquor: 0.3%
Ammonium sulphate: 0.1%
Casein: 0.5%
Potassium hydrogen phosphate: 0.01%
in tap water After sterilization at 120° C for 20 minutes in an autoclave, the pH was 7.
Productive medium:
Dextrin: 3%

Calcium carbonate: 0.6%
Corn steep liquor: 0.6%
Casein: 0.5%
Ammonium sulphate: 0.1%
Potassium hydrogen phosphate: 0.01%
The pH after sterilization was 7.

The sterilization is carried out as described for the vegetative medium. The same activity, 65 µg/ml, is achieved after 130 hours.

EXAMPLE 4

500 ml of the vegetative liquid medium described in Example 1 contained in a 2000 ml glass flask are inoculated with a culture of Streptomyces 1762 on solid medium, as described in Example 2.

The mixture is incubated at 28° C for 48 hours on a rotary shaker with a stroke of 70 mm at 120 r.p.m. 100 ml of the culture broth so obtained serve to inoculate 3000 ml of the same liquid medium contained in a 5-liter neutral glass fermenter, provided with a screw-stirrer, an inlet tube for bubbling air ending under the screw-stirrer, a breakwater device, a tube for inoculation, an air outlet tube, temperature-checking equipment, and a device for intermittent or continuous additions under sterile conditions. Growth is carried out under shaking with a rate of 400 r.p.m. at 28° C, with an aeration rate of 3 liters per minute.

After 24 hours, 300 ml of the broth culture thus incubated serve to inoculate 6 liters of the productive medium described in Example 1 contained in a 10-liter neutral glass fermenter like that described above. During the fermentation, carried out at a stirring rate of 350 r.p.m. and with an aeration rate of 5 liters per minute, foaming is checked by adding small amounts of silicone antifoaming agent. The highest production obtained in 150 hours of fermentation corresponded to a 60 µg/ml concentration of F.I. 1762.

EXAMPLE 5

The process differs from that described in Example 4 only in that the productive medium was inoculated with 600 ml of the vegetative culture medium instead of 300 ml of the same. The maximum yield of F.I. 1762 has been obtained at the 140th hour with 70 µg/ml.

EXAMPLE 6

The culture liquid resulting from the fermentation of 50 liters and obtained according to Example 4, is mixed with an absorbent siliceous earth material and filtered from the mycelium. The cake and the filtrate obtained are extracted separately. The cake is suspended in acetone, diluted with 0.4N aqueous sulphuric acid, and stirred for 2 hours. The liquid suspension is filtered and the cake is further stirred twice. The extracts thus obtained are neutralized and the acetone is evaporated in vacuo. The resulting suspension is then filtered. The solid obtained is shaken repeatedly with acidified water (pH 3) and refiltered. The filtrate is adjusted to pH 8.6 and extracted thoroughly with n-butanol. The butanolic extracts are combined and concentrated to a small volume in vacuo. To this solution, two volumes of ethyl ether are added and the product is reextracted from the organic phase with 0.1M hydrochloric acid. The extraction is repeated several times until the aqueous phase appears red-yellow colored. The combined aqueous extracts are adjusted to pH 8.6 and extracted three times with chloroform. The chloroform extracts are combined, dried over anhydrous sodium sulphate, filtered, whereupon a few drops of hydrochloric acid in anhydrous methanol are added to clarify the solution, which finally is concentrated to a small volume. During the concentration needle-shaped red crystals separate and are collected from the solution by filtration. The product thus obtained (0.3 g) on analysis is the hydrochloride of the antibiotic. The mother liquor is concentrated and the addition of some ethyl ether causes the precipitation of further 0.13 g of crude product containing F.I. 1762.

The filtrate is adjusted to pH 8.6 and extracted with n-butanol. The operation is carried out twice. The combined organic phases concentrated to a small volume and mixed with two volumes of ethyl ether, are reextracted with 0.1N hydrochloric acid. The combined aqueous phases are adjusted to pH 8.6 and extracted three times with chloroform. The chloroform solution is dried over anhydrous sodium sulphate and treated with a few drops of hydrochloric acid in anhydrous methanol and concentrated to a small volume. From the concentrated solution, by adding some ethyl ether, 0.35 g of F.I. 1762 separates as crude hydrochloride, which contains the aglycone.

By operating as above indicated, but using sulphuric acid in methanol instead of hydrochloric acid, the antibiotic F.I. 1762 may be obtained as the sulphate.

EXAMPLE 7

A 45-liter culture broth, obtained according to Example 4, is filtered from the mycelium by help of the usual adsorbent siliceous earth materials. The cake is suspended in n-butanol and extracted with this solvent three times. Finally the cake is discarded and the extracts concentrated to a small volume in vacuo. Three volumes of ether are added to the organic phase which is extracted several times with water containing 5% of acetic acid. The aqueous extracts are adjusted to pH 8.6 and reextracted with chloroform. The chloroform extract is dried over anhydrous sodium sulphate and concentrated to a small volume in vacuo. A few drops of hydrochloric acid in anhydrous methanol are added and the product is precipitated with ether. A solid constituted by the crude hydrochloride of the antibiotic F.I. 1762 is obtained.

By employing sulphuric acid instead of hydrochloric acid the corresponding sulphate may be obtained. The ether-chloroform solutions still contain several pigments, which may be extracted with 1N sodium hydroxide solution, but the nature of which has not yet been investigated.

EXAMPLE 8

The usual adsorbent siliceous materials are added to 12 liters of a broth culture obtained according to Example 4, and the whole is then filtered. The mycelium cake is shaken three times with three liters of a solution consisting of acetone and 0.5N hydrochloric aicd in the ratio of 3 parts of acetone and two parts of acid. The resulting extract is neutralized and acetone is eliminated in vacuo. The solid separated is filtered and the filtrate is adjusted to pH 8.6, and extracted thoroughly with butanol until the butanol extract appears red-colored. It is concentrated to a small volume in vacuo; a volume of petroleum ether is added and it is extracted with aqueous 0.1N hydrochloric acid in small portions. The aqueous extracts are combined, adjusted to pH 8.6, and reextracted with chloroform until this appears red-colored. The combined chloroform extracts are dried over anhydrous sodium sulphate and concentrated to a small volume. A few drops of hydrochloric acid in anhydrous methanol are added and the product is precipitated with ethyl ether. 1.2 g of crude hydrochloride of F.I. 1762 are obtained.

By employing sulphuric acid instead of hydrochloric acid the corresponding sulphate may be obtained.

EXAMPLE 9

1 g of the crude material containing F.I. 1762 is submitted to the countercurrent distribution in a 40-tube Craig apparatus, employing an n-butanol: phosphate buffer at pH 5.2. 25 cc of each phase for each tube are used. Upon having carried out the necessary number of transfers, checking spectrophotometrically at 500 m$\mu$ the contents of the different tubes, two intervals containing high quantities of the substances are defined. One interval corresponds to tubes 7–21, the other corresponds to tubes 32–39. The intermediate tubes show also the presence of components containing colored substances and are stored separately. The tubes 7–21 are combined, the organic phase separated and the aqueous phase adjusted to pH 8.5 with a normal solution of sodium hydroxide. The aqueous phase is then extracted twice with n-butanol, the organic extracts combined and concentrated under reduced pressure to a small volume. Three volumes of ether are added and the solution extracted with small portions of dilute hydrochloric acid until the portions become colored. The aqueous phase is then adjusted to pH 8.6 and extracted with chloroform. The chloroform extract is dried and treated with a few drops of hydrochloric acid in anhydrous methanol until the solution becomes clear. It is then concentrated at low temperature (<35° C) in vacuo. On concentration the F.I. 1762 precipitates as the hydrochloride in crystalline form. Yield 0.125 g.

By employing sulphuric acid instead of hydrochloric acid the corresponding sulphate is obtained.

From the tubes 32–39, in which the colored substances are revealed by paper chromatography to be the aglycone, by combining the upper phases, adding an equal volume of ehter and extracting with a normal soda solution, a color turning from red to blue-violet is noticed and the transfer of the coloring into the aqueous solution is achived. The extraction with soda is carried out twice. On acidifying the alkaline extracts with hydrochloric acid, a red product precipitates on crystallization from n-butanol is shown to be the aglycone of the antibiotic F.I. 1762 by chromatographic analysis, spectro-photometric examination in the U.V., in the visible and in the I.R. ranges and by the melting point.

EXAMPLE 10

2 g of the crude material containing 10% of the pigments constituted by the antibiotic F.I. 1762 and by its aglycone, checked through the intensity of the adsorption maxima in the visible range, are dissolved in 150 cc of water and adjusted to neutral pH. The insoluble portion is filtered and the aqueous solution is extracted several times with ether. On evaporation in vacuo to dryness 20 mg of a red solid are obtained, which by paper-chromatographic analysis is shown to be the aglycone of the antibiotic F.I. 1762. To the aqueous phase 40 cc of an aqueous saturated solution of picric acid are added. A red-yellowish precipitate of the picrate of the antibiotic F.I. 1762 is formed.

EXAMPLE 11

On treating the sulphate of the antibiotic F.I. 1762 with a solution of calcium pantothenate, the pantothenate of the antibiotic F.I. 1762 is obtained by double decomposition.

EXAMPLE 12

1 g of F.I. 1762 hydrochloride is dissolved in 50 cm$^3$ of 0.2N HCl and kept at 90° C for 60 minutes. Red flakes separate. After cooling, it is extracted with n-butanol and the pigment passes into the organic phase. The aqueous acidic phase is treated separately as hereinbelow indicated whilst the butanol extracts are washed with water and evaporated in vacuo to dryness. The residue, 0.680 g on recrystallization from hot methyl-isobutyl-ketone gives red needle-shaped brilliant crystals of the aglycone of the antibiotic; m.p. 213°–214° C; $[\alpha]_D^{25} = +193°$ (c = 0, 1 dioxane). At the paper chromatography (system n.butanol saturated with aqueous phosphate buffer at pH 52) the aglycone shows Rf = 0.85. Empirical formula $C_{21}H_{18}O_8$. The pH of the aqueous acidic phase is adjusted to 5.6 by percolation through Dowex 1 × 4 (50–100 mesh); OH-form), whereupon the aqueous phase is evaporated in vacuo to dryness, the residue dissolved in ethanol, decolorized with Darco G-60. On addition of acetone, white needle crystals of amino-sugar hydrochloride separate. The precipitate was collected (g 0.280), recrystallized from ethanol-acetone and dried over $P_2O_5$; m.p. 168° C (dec.); $[\alpha]_D^{25} = -54.5°$ (c = 1 $H_2O$). Empirical formula $C_6H_{13}O_3N \cdot HCl$.

At the paper chromatography system n-butanol: acetic acid : water (2 : 1 : 1) it shows Rf =;0 0.70.

PHARMACOLOGY

STUDY OF THE ANTITUMOR ACTIVITY OF THE ANTIBIOTIC F.I. 1762

The study of the antitumor activity of the antibiotic F.I. 1762 obtained from the Streptomyces 1762 has been carried out on a "spectrum" of mouse and rat tumors, both in solid and ascitic form. At least 20 animals per lot were used.

1. Ascitic tumors

Activity tests were carried out on mice, bearing Ehrlich ascitic carcinoma and on rats, which are grafted with hepatoma AH 130 and Oberling-Guerin-Guerin myeloma.

a. Ehrlich ascitic carcinoma

Mice are grafted intraporitoneally with a suspension of tumor cells and treated with solutions of different concentrations of the antibiotic for five consecutive days starting from the day following the tumor implantation. Table III, where the obtained results are summarized, shows that the antibiotic under examination, administered in equal doses of 1.75 and 1.25 mg/kg/day, has a remarkable inhibitory effect on the ascitic tumor growth and has increased considerably the average survival rate of the treated animals.

TABLE III

| Lots | Dose mg/kg/day | Ehrlich ascitic carcinoma Body weight increase in grams (days after the implantation) | | | Average survival time (days) |
| --- | --- | --- | --- | --- | --- |
| | | 7 | 14 | 21 | |
| Controls | — | +9.6 | +21.4 | — | 16.4 |
| F.I. 1762 | 1.75 | +1.3 | +2.4 | +4.7 | 36.4 |

TABLE III-continued

| Lots | Dose mg/kg/day | Ehrlich ascitic carcinoma Body weight increase in grams (days after the implantation) | | | Average survival time (days) |
| --- | --- | --- | --- | --- | --- |
| | | 7 | 14 | 21 | |
| F.I. 1762 | 1.25 | +1.5 | +3.1 | +4.4 | 32.0 |
| F.I. 1762 | 0.75 | +2.9 | +5.3 | — | 18.8 |

The result has been confirmed by a successive experiment in which the antibiotic has been administered at the dose of 1.75 mg/kg intravenously for 4 days (Table IV).

TABLE IV

| Lots | Dose mg/kg/day | Ehrlich ascitic carcinoma Body weight increase in grams (days after implantation) | | Average survival time (days) |
| --- | --- | --- | --- | --- |
| | | 7 | 12 | |
| Controls | — | +6.3 | +14.2 | 12.4 |
| F.I. 1762 | 1.75 | +0.1 | +2.2 | 35.1 | b. Hepatoma AH 130

Wistar rats, grafted with accitic hepatoma have been treated intraperitoneously for 5 consecutive days with antibiotic doses of 2 and 1 mg/kg/day. While the control animals (non-treated) had an average survival time of 11.8 days after the tumor implantation, all the treated rats were still alive after 50 days of the experiment. In none of them was any trace of tumor noticed.

c. Ascitic myeloma

This experiment was carried out on Wister rats, which have been grafted with a suspension of tumor cells and then have been treated intraperitoneously with a solution of the antibiotic according to the following scheme: one group three times on alternate days with a dose equal to 2 mg/kg/day; another group for 5 consecutive days with a dose of 1 mg/kg/day. Under these conditions, a delay in the diffusion of the tumor has been observed, which is ascribed to the increase of average survival rate of the animals treated in comparison with the controls (Table V).

Table V

| Lots | Ascitic myeloma | | Average survival time (days) |
| --- | --- | --- | --- |
| | Dose mg/kg/day | For treatment | |
| Controls | — | — | 10.7 |
| F.I. 1762 | 2 | 3 | 17.7 |
| F.I. 1762 | 1 | 5 | 16.7 |

2. Solid tumors

The checking of the activity on solid tumors has been carried out with Ehrlich adenocarcinoma and sarcoma 180 in the mouse and with Walker carcinosarcoma and the Oberling-Guerin-Guerin myeloma in the rat.

a. Ehrlich adenocarcinoma

Mice grafted with a fragment of tumor subcutaneously for 6 days starting from the day after the transplantation have been treated with a solution of the antibiotic. At the eighth day of experiment all the animals were killed and the tumor was removed and weighed. The results thus achieved are summarized in Table VI.

Table VI

| Lots | Dose mg/kg/day | Ehrlich adenecarcinoma | | | | |
| --- | --- | --- | --- | --- | --- | --- |
| | | Body weight change (grams) | | Mortality | Average tumor weight (grams) | % Inhibition |
| | | gross | not | | | |
| Controls | — | +4.85 | +2.27 | 0/10 | 2.583 | — |
| F.I. 1762 | 6 | +2.59 | +1.07 | 0/10 | 1.522 | 41.1 |
| F.I. 1762 | 3 | +3.84 | +1.59 | 0/10 | 2.253 | 12.- |

The antibiotic at the dose of 6 mg/kg/day has an inhibition of the tumor growth equal to 41.1%.

b. Sarcoma 180

Mice grafted with a fragment of neoplastic tissue have been treated intraperitoneally for seven consecutive days, starting from the day following the tumor implantation. The antibiotic was administered in solution at a dose of 2 mg/kg/day. At the tenth day of experiment, all the mice were killed and the tumors and spleens were removed. The results reported in Table VII show that in this experiment also the treatment with the antibiotic caused a marked inhibition of tumor growth and a marked shrinkage of the spleen.

Table VII

| Lot and Dose | mg/kg/day | Sarcoma 180 | | | | | | |
| --- | --- | --- | --- | --- | --- | --- | --- | --- |
| | | Body weight change (grams) | | Mortality | Average Weight | | % Inhibition | |
| | | gross | not | | tumor grams | spleen milligrams | tumor | spleen |
| Controls | — | +5.05 | +2.83 | 0/10 | 2.225 | 251 | — | — |
| F.I. 1762 | 2 | −1.72 | −3.01 | 0/10 | 1.289 | 93.5 | 42.1 | 62.7 | c. Walker carcinosarcoma

The rats grafted with this tumor have been treated intravenously 8 times within 10 days; at the 11th day of experiment, the surviving animals were killed and the tumors removed. The results are summarized in the following Table VIII:

Table VIII

| Lots and Dose | mg/kg/day | Walker carcinosarcoma Body weight change (grams) gross | not | Mortality | Average tumor weight (grams) | % Inhibition |
|---|---|---|---|---|---|---|
| Controls | — | +22.9 | +6.96 | 1/10 | 15.940 | — |
| F.I. 1762 | 1 | +10.2 | +0.76 | 1/10 | 9.443 | 42.1 |
| F.I. 1762 | 2 | +27.9 | +22.25 | 1/10 | 5.404 | 66.1 |

The antibiotic showed a marked inhibitory effect also on this type of tumor especially with a dose of 2 mg/kg/day which was tolerated when intravenously injected.

A second experiment with rats, bearing the same tumor, has been carried out to investigate the effect of the antibiotic on the animals' survival besides the antitumor activity. In this case the rats were treated intravenously 8 times within 12 days at the dose of 3 mg/kg/day. The results, reported in the following Table, confirm the inhibitory effect of the antibiotic on the tumor growth and show that by such a treatment the average survival of the rats has increased by 50.8%.

Table IX

| Lots and Dose | mg/kg/day | Walker carcinosarcoma Tumor growth inhibition (% of the control) 9th day | 29th day | Average survival time (days) |
|---|---|---|---|---|
| Controls | — | | | 16.9 |
| F.I. 1762 | 3 | 71.0 | 31.6 | 25.5 |

The tumor growth inhibition is considerable during the treatment, but still continues in a remarkable degree 20 days after the injections were stopped.

d. Oberling-Guerin-Guerin myeloma

Long-Evans rats grafted with a fragment of tumor tissue have been treated intravenously for 10 days, starting from the day following the tumor implantation. The surviving animals were killed the 13th day of experiment and the tumors were removed and weighed.

Table X

| Lots and Dose | mg/kg/day | O.G.G. myeloma Body weight change (grams) gross | not | Mortality | Average tumor weight (grams) | % Inhibition |
|---|---|---|---|---|---|---|
| Controls | — | +45.2 | +28.— | 3/12 | 17.23 | — |
| F.I. 1762 | 2 | +33.3 | +20.— | 0/12 | 11.30 | 34.5 |
| F.I. 1762 | 4 | +3.8 | +0.8 | 4/12 | 2.98 | 82.8 |

These results have been confirmed again in a successive experiment in which the animals have been treated intravenously 7 times within 14 days with an antibiotic solution at the dose of 2.5 mg/kg/day.

Table XI

| Lots and Dose | mg/kg/day | O.G.G. myeloma Body weight change (grams) gross | not | Mortality | Average weight tumor grams | spleen grams | % Inhibition tumor | spleen |
|---|---|---|---|---|---|---|---|---|
| Controls | — | +53.7 | +40.22 | 5/15 | 13.486 | 1.303 | — | — |
| F.I. 1762 | 2.5 | +20.9 | +16.79 | 5/15 | 4.114 | 0.598 | 69.5 | 54.1 |

Tables X and XI show that the antibiotic is active also against this kind of tumor; the doses of 2 mg and 2.5 mg/kg/day intravenously produced the best results regarding the antitumor activity as well as the good tolerance of the antibiotic.

We claim:

1. A process for the preparation of a new antibiotic F.I. 1762, which comprises cultivating the Streptomyces 1762 under aerobic conditions in a liquid nutrient medium containing a carbon source, a nitrogen source and mineral salts, at a temperature between 25° and 37° C, over a period of time from 3 to 7 days, and extracting the formed antibiotic from the fermentation broth at a pH between 8 and 9 by means of a water-immiscible solvent, isolating and purifying the antibiotic F.I. 1762.

2. A process for the preparation of the acid addition salts of antibiotic F.I. 1762, which comprises cultivating the Streptomyces 1762 under aerobic conditions in a liquid nutrient medium containing a carbon source, a nitrogen source and mineral salts, at a temperature between 25° and 37° C, over a period of time from 3 to 7 days, and extracting the formed antibiotic from the fermentation broth at a pH between 8 and 9 by means of a water-immiscible solvent, adding an acid to form the acid addition salt of antibiotic F.I. 1762, and isolating the latter.

3. A process for the preparation of the aglycone of the antibiotic F.I. 1762, which comprises cultivating the Streptomyces 1762 under aerobic conditions in a liquid nutrient medium containing a carbon source, a nitrogen source and mineral salts, at a temperature between 25° and 37° C, over a period of time from 3 to 7 days, and extracting the formed antibiotic from the fermentation broth at a pH between 8 and 9 by means of a water-immiscible solvent, hydrolyzing with a dilute mineral acid to form a reducing sugar and a neutral aglycone of F.I. 1762 and separating the latter.

* * * * *